United States Patent [19]

Michelotti et al.

[11] Patent Number: 6,140,362
[45] Date of Patent: *Oct. 31, 2000

[54] METHOD FOR INHIBITING THE GROWTH OF MAMMALIAN CELLS

[75] Inventors: Enrique Luis Michelotti, Fort Washington; David Hamilton Young, Ambler, both of Pa.

[73] Assignee: Rohm and Haas Company, Philadelphia, Pa.

[*] Notice: This patent issued on a continued prosecution application filed under 37 CFR 1.53(d), and is subject to the twenty year patent term provisions of 35 U.S.C. 154(a)(2).

[21] Appl. No.: 08/939,516

[22] Filed: Sep. 29, 1997

Related U.S. Application Data

[60] Provisional application No. 60/027,583, Oct. 3, 1996.

[51] Int. Cl.[7] .......................... A61K 31/21; A61K 31/26; A61K 31/275; A61K 31/165; A61K 31/15
[52] U.S. Cl. ......................... 514/514; 514/519; 514/617; 514/619; 514/640
[58] Field of Search ...................... 514/514, 519, 514/617, 619, 640

[56] References Cited

U.S. PATENT DOCUMENTS

| | | | |
|---|---|---|---|
| 3,661,991 | 5/1972 | McNulty et al. | 260/558 D |
| 4,264,596 | 4/1981 | Miyashita et al. | 424/248.54 |
| 4,371,533 | 2/1983 | Akimoto et al. | 424/248.54 |
| 4,515,785 | 5/1985 | Shimizu et al. | 424/195.1 |
| 4,596,676 | 6/1986 | Cullinan | 530/391 |
| 4,675,400 | 6/1987 | Cullinan | 514/283 |
| 4,701,406 | 10/1987 | Chou | 435/7 |
| 4,707,498 | 11/1987 | Kolb et al. | 514/671 |
| 4,822,902 | 4/1989 | Carley et al. | 558/14 |
| 4,863,940 | 9/1989 | Sharma | 514/359 |
| 4,904,697 | 2/1990 | Sunkara et al. | 514/629 |
| 4,950,761 | 8/1990 | Temple, Jr. | 546/308 |
| 5,003,056 | 3/1991 | Nishikiori et al. | 536/71 |
| 5,254,584 | 10/1993 | Michelotti et al. | 514/514 |
| 5,304,572 | 4/1994 | Michelotti et al. | 514/514 |
| 5,376,685 | 12/1994 | Stanek et al. | 514/583 |

OTHER PUBLICATIONS

Duanmu, C. et al., Tubulin–dependent Hydrolysis of Guanosine Triphosphate as a Screening Test to Identify New Antitubulin Compounds as Antimitotic Agents: Application to Carbamates of Aromatic Amines, *Cancer Research*, 49, 1989, 1344–1348.

McGown, A.T. et al., Interaction of the Novel Agent Amphethinile with Tubulin, *Br. J. Cancer*, 59, 1989, 865–868.

Jiang, J.B. et al., Synthesis and Biological Evaluation of 2–Styrylquinazolin–4(3H)–ones, a New Class of Antimitotic Anticancer Agents Which Inhibit Tubulin Polymerization, *J. Med. Chem.*, 33, 1990, 1721–1728.

Hargreaves, Alan J. et al., Inhibition by p–bromphenacyl bromide of Microtubule Assemby In Vitro, *Biochemical Society Transactions*, 19, 1991, 1140–1143.

Batra, Janendra K. et al., Methylenedioxy–benzopyran, Analogs of Podophyllotoxin, A New Synthetic Class of Antimitotic Agents that Inhibit Tubulin Polymerization, *Biochemical Pharmacology*, vol. 37, No. 13, 1988, 2595–2602.

*MT and MT Poisons in Pathology and Medicine*, §11.3, Date unknown but believed to be prior to Sep. 29, 1997.

*Primary Examiner*—Jerome D. Goldberg
*Attorney, Agent, or Firm*—Thomas D. Rogerson

[57] ABSTRACT

A method for inhibiting mammalian cell growth is disclosed. The method uses compounds known as N-acetonylarylamides. The compounds have been shown to inhibit cell mitosis and to inhibit microtubule assembly. The method may be used to treat diseases associated with rapid cell growth, particularly cancer. The compounds used in the method of the present invention may be used in combination with other therapies and may be administered by known techniques for drug administration.

5 Claims, No Drawings

METHOD FOR INHIBITING THE GROWTH OF MAMMALIAN CELLS

This appln claims benefit of U.S. Provisional No. 60/027,583 filed Oct. 3, 1996.

The present invention relates to a method for inhibiting the growth of mammalian cells. In particular, the present invention relates to a method for inhibiting the growth of cancer cells by the use of certain N-acetonylarylamide derivatives.

Cells reproduce by division into two daughter cells. The DNA replication phase of the cell reproduction cycle is known as the "S phase". During the S-phase, chromosomes within a cell are replicated, yielding pairs of identical daughter DNA molecules known as sister chromatids, which then separate during mitosis to produce two new nuclei. Although the term "mitosis" is commonly used synonomously with the term "cell division", mitosis correctly refers to only one phase of the cell division process: the process in which the sister chromatids are partitioned equally between the two daughter cells. In eukaryotic cells, mitosis is followed by cytokinesis, which is the process by which the cell cytoplasm is cleaved into two distinct but genetically identical daughter cells.

At the onset of mitosis, small intracellular filamentous structures known as cytoplasmic microtubules, of which the major component is a protein called tubulin, disassemble into tubulin molecules. The tubulin then reassembles into microtubules forming an intracellular structure known as the "mitotic spindle". The mitotic spindle plays a critical role in distributing chromosomes within the dividing cell precisely between the two daughter nuclei.

Cancer cells are characterized by more rapid cell division and proliferation than observed in most healthy cells, and many anti-cancer agents operate by inhibiting cell division. Since cancer cells divide more rapidly than do healthy cells, cancer cells are preferentially killed by anti-cancer agents which inhibit mitosis. Such compounds are called "antimitotic".

Several classes of antimitotic compounds are known which, when administered to dividing cells, prevent the formation of the mitotic spindle by binding to tubulin or microtubules. Absence of a mitotic spindle results in the arrest of mitosis and an accumulation of cells with visible sister chromatids, but without normal mitotic figures. Inability of the cells to divide ultimately results in cell death. Such compounds are discussed in, for example, E. Hamel, *Medicinal Research Reviews*, vol. 16, pp. 207–231 (1996). Examples of compounds which are known to prevent the formation of a mitotic spindle include the Catharalthus alkaloids vincristine and vinblastine; benzimidazole carbamates such as nocodazole; colchicine and related compounds such as podophyllotoxin, steganacin and combretastatin; and taxanes such as paclitaxel and docetaxel. The alkaloids vincristine and vinblastine have been used as anticancer drugs, as have been the taxane-based compounds (see, for example, E. K. Rowinsky and R. C. Donehower, *Pharmacology and Therapeutics*, vol. 52, pp. 35–84 (1991)).

There continues to be a need for new anti-cancer drugs. Accordingly, the present invention provides a method for inhibiting the growth of cells, including cancer cells, by the use of certain compounds known as N-acetonylarylamides. The compounds used in the method of the present invention are known to be fungicidally active. The compounds and their use in fungicidal applications are discussed in U.S. Pat. Nos. 3,661,991; 4,822,902; 4,863,940; 5,254,584; and 5,304,572. It has been surprisingly discovered that these compounds interact with mammalian cell microtubules. It has been discovered that these compounds also inhibit the growth of cancer cells.

A first aspect of the present invention is a method for inhibiting mammalian cell growth comprising the use of compounds having the structural formula:

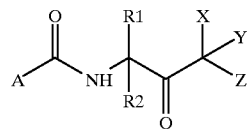

I wherein:

A is selected from phenyl, pyridyl, furyl, thienyl, isoxazolyl, oxazolyl, pyrrolyl, isothiazolyl, thiazolyl, pyrazolyl, imidazolyl, pyrimidinyl, quinolyl, isoquinolyl, naphthyl, pyridazinyl, pyrazinyl, benzothienyl, indolyl, benzofuranyl, or benzyl, any of which may be substituted with up to four substituents, each independently selected from halo, cyano, $(C_1-C_6)$alkyl, halo$(C_1-C_6)$alkyl, $(C_2-C_6)$alkenyl, $(C_2-C_6)$alkynyl, $(C_1-C_6)$alkoxyl, halo$(C_1-C_6)$alkoxyl, nitro, —$NR^6R^7$, —$CR^8$=$NOR^9$, $NHCOOR^{10}$, —$CONR^{11}R^{12}$, and —$COOR^{13}$; or from $(C_3-C_7)$cycloalkyl, $(C_1-C_6)$alkyl, $(C_1-C_6)$alkylthio, halo$(C_1-C_6)$alkyl, $(C_2-C_6)$alkenyl, $(C_2-C_6)$alkynyl, $(C_1-C_6)$alkoxyl, or halo$(C_1-C_6)$alkoxyl;

$R^1$ and $R^2$ are each independently selected from H, $(C_1-C_6)$alkyl, halo$(C_1-C_6)$alkyl, $(C_2-C_6)$alkenyl, and $(C_2-C_6)$alkynyl, provided that at least one of $R^1$ and $R^2$ is not H;

$R^6$ and $R^7$ are each independently selected from H, $(C_1-C_6)$alkyl, and $(C_1-C_6)$alkylcarbonyl;

$R^8$ is selected from H, $(C_1-C_6)$alkyl, $(C_2-C_6)$alkenyl, and $(C_2-C_6)$alkynyl;

$R^9$ is selected from H, $(C_1-C_6)$alkyl, $(C_2-C_6)$alkenyl, $(C_2-C_6)$alkynyl, and $(C_1-C_4)$alkylcarbonyl;

$R^{10}$ is selected from H, $(C_1-C_6)$alkyl, $(C_2-C_6)$alkenyl, and $(C_2-C_6)$alkynyl;

$R^{11}$ and $R^{12}$ are each independently selected from H, $(C_1-C_6)$alkyl, $(C_2-C_6)$alkenyl, and $(C_2-C_6)$alkynyl;

$R^{13}$ is selected from H, $(C_1-C_6)$alkyl, $(C_2-C_6)$alkenyl, and $(C_2-C_6)$alkynyl; and X, Y and Z are each independently selected from H, halo, cyano, thiocyano, isothiocyano and $(C_1-C_6)$alkylsulfonyloxy, provided that at least one of X, Y and Z is halo, cyano, thiocyano, isothiocyano or $(C_1-C_6)$alkylsulfonyloxy.

When A is substituted with two or more substituents, two substituents may form a fused 5, 6, or 7 membered ring, which may contain one or more heteroatoms.

As used herein, the term "halo" means fluoro, bromo, chloro, or iodo.

The term "alkyl" means a straight or branched saturated hydrocarbon group having from 1 to 6 carbons per group, and includes, e.g. methyl, ethyl, n-propyl, isopropyl, n-butyl, isobutyl, t-butyl, pentyl and hexyl. Halo-substituted alkyl groups, referred to as haloalkyl, include, for example, chloromethyl, trifluoromethyl, bromoethyl, pentafluoroethyl, iodopropyl, and chlorobutyl.

The term "$(C_2-C_6)$alkenyl" means a straight or branched group having at least one double bond and from 2 to 6 carbons per group, and includes, e.g, ethenyl, 2-propenyl, 2-butenyl and 2-methyl-2-propenyl.

The term "$(C_2-C_6)$alkynyl" means a straight or branched alkynyl group having at least one triple bond and from 2 to 6 carbons per group, and includes, e.g, ethynyl, 2-propynyl and 2-butynyl.

The term "($C_1$–$C_6$)alkoxyl" means a straight or branched alkoxyl having from 1 to 6 carbons per group, and includes, e.g, methoxyl, propoxyl, n-butoxyl and t-butoxyl.

The term "($C_1$–$C_6$)alkylthio" means a straight or branched alkylthio group having from 1 to 6 carbons per group, and includes, e.g., methylthio and propylthio.

Alkyl, alkenyl, alkynyl, alkoxyl and alkylthio groups may optionally be substituted with from 1 to 5 halogen atoms, unless otherwise specified.

The term "($C_3$–$C_7$) cycloalkyl" includes, for example, cyclopropyl and cyclohexyl.

The term "($C_1$–$C_6$)alkylcarbonyl" includes, for example, methylcarbonyl and butylcarbonyl.

The term "($C_1$–$C_6$)alkylsulfonyloxy" includes, for example methylsulfonyloxy and propylsulfonyloxy.

Suitable —$NR_6R_7$ moieties include amino, monosubstituted amino and disubstituted amino such as, for example, amino, methylamino, ethylamino, acetylamino, and diethylamino.

The term "nitro" means a group having the structural formula —$NO_2$.

The term "cyano" means a group having the structural formula —CN.

The term "thiocyano" means a group having the structural formula —SCN.

The term "isothiocyano" means a group having the structural formula —NCS.

Suitable —$CR_8$=$NOR_9$ moieties include, for example, hydroximinomethyl, methoxyiminomethyl, ethoxyiminomethyl, methoxyiminoethyl, and methylcarbonyloxyiminomethyl.

Suitable —$CONR^{11}R^{12}$ substituents include amido (—$CONH_2$), monosubstituted amido and disubstituted amido such as, for example, methylamido (—$CONHCH_3$), dimethylamido (—$CON(CH_3)_2$), propylamido, and dibutylamido.

Suitable $NHCOOR^{10}$ substituents include, for example, methylcarbamate and isopropylcarbamate.

In a preferred embodiment of the method of the present invention, using compounds having the structural formula (I), A is phenyl and the compounds have the structural formula:

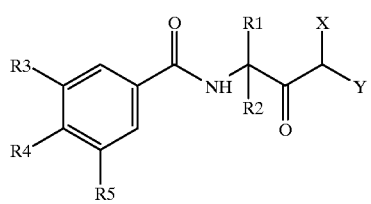

(II)

wherein:

$R^1$ and $R^2$ are H, ($C_1$–$C_6$)alkyl, halo($C_1$–$C_6$)alkyl, ($C_2$–$C_6$)alkenyl, and ($C_2$–$C_6$)alkynyl, provided that at least one of $R^1$ and $R^2$ is not H; $R^3$, $R^4$, and $R^5$ are each independently selected from H, halo, cyano, ($C_1$–$C_6$)alkyl, halo($C_1$–$C_6$)alkyl, ($C_2$–$C_6$)alkenyl, ($C_2$–$C_6$)alkynyl, ($C_1$–$C_6$)alkoxyl, ($C_1$–$C_6$)alkylthio, halo($C_1$–$C_6$)alkoxyl, nitro, carboxyl, —$NR^6R^7$, —$CR^8$=$NOR^9$, $NHCOOR^{10}$, —$CONR^{11}R^{12}$, and —$COOR^{13}$, $R^6$, $R^7$, $R^8$, $R^9$, $R^{10}$, $R^{11}$, $R^{12}$, and $R^{13}$, are H or ($C_1$–$C_6$)alkyl, and X and Y are each independently selected from H, halo, cyano, thiocyano, isothiocyano and ($C_1$–$C_6$)alkysulfonyloxy, provided that at least one of X and Y is not H.

In a particularly preferred embodiment of the method of the present invention, the compounds used have the structural formula (II), wherein X is chloro; Y is H; $R^1$ is methyl; $R^2$ is selected from methyl and ethyl; $R^3$ and $R^5$ are each independently selected from H, halo, methyl, nitro, cyano, —$NR^6R^7$, —$CR^8$=$NOR^9$ and —$NHCOOR^{10}$ and $R^4$ is selected from H, —$NR^6R^7$, cyano, —$CR^8$=$NOR^9$, —$NHCOOR^{10}$, $COOR^{13}$, and ($C_1$–$C_4$)alkyl; and $R^6$, $R^7$, $R^8$, $R^9$, $R^{10}$ and $R^{13}$ are H or ($C_1$–$C_6$)alkyl.

In an even more preferred embodiment of the method of the present invention, the compounds have the structural formula (II), wherein X is chloro, Y is H. $R^1$ is methyl, $R^2$ is ethyl, $R^3$ is halo or cyano, $R^4$ is amino or $CHNOCH_3$ and $R^5$ is amino or $CHNOCH_3$, provided that $R^4$ and $R^5$ are not the same.

Also contemplated for use in the method of the present invention are compounds having the structural formula (II) wherein $R^4$ and $R^5$ together form a fused 5, 6, or 7-membered ring, which may contain up to two heteroatoms selected from the group consisting of O, S, N, and P; $R^1$ and $R^2$ are H, ($C_1$–$C_6$)alkyl, halo($C_1$–$C_6$)alkyl, ($C_2$–$C_6$)alkenyl, and ($C_2$–$C_6$)alkynyl, provided that at least one of $R^1$ and $R^2$ is not H; $R^3$ is selected from H, halo, cyano, ($C_1$–$C_6$)alkyl, halo($C_1$–$C_6$)alkyl, ($C_2$–$C_6$)alkenyl, ($C_2$–$C_6$)alkynyl, ($C_1$–$C_6$)alkoxyl, ($C_1$–$C_6$)alkylthio, halo($C_1$–$C_6$)alkoxyl, nitro, carboxyl, —$NR^6R^7$, —$CR^8$=$NOR^9$, $NHCOOR^{10}$, —$CONR^{11}R^{12}$, and —$COOR^{13}$, $R^6$, $R^7$, $R^8$, $R^9$, $R^{10}$, $R^{11}$, $R^{12}$, and $R^{13}$ are H or ($C_1$–$C_6$) alkyl, and X and Y are each independently selected from H, halo, cyano, thiocyano, isothiocyano and ($C_1$–$C_6$)alkysulfonyloxy, provided that at least one of X and Y is not H.

In an alternative embodiment of the method of the present invention, using compounds having the structural formula (I), A is 4-pyridyl and the compounds have the structural formula:

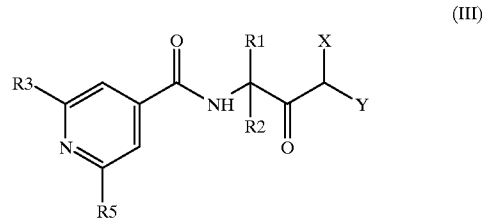

(III)

wherein $R^1$ and $R^2$ are H, ($C_1$–$C_6$)alkyl, halo($C_1$–$C_6$)alkyl, ($C_2$–$C_6$)alkenyl, and ($C_2$–$C_6$)alkynyl, provided that at least one of $R^1$ and $R^2$ is not H; $R^3$ and $R^5$ are each independently selected from H, halo, cyano, ($C_1$–$C_6$)alkyl, halo($C_1$–$C_6$) alkyl, ($C_2$–$C_6$)alkenyl, ($C_2$–$C_6$)alkynyl, ($C_1$–$C_6$)alkoxyl, ($C_1$–$C_6$)alkylthio, halo($C_1$–$C_6$)alkoxyl, nitro, carboxyl, —$NR^6R^7$, —$CR^8$=$NOR^9$, $NHCOOR^{10}$, —$CONR^{11}R^{12}$, and —$COOR^{13}$, $R^6$, $R^7$, $R^8$, $R^9$, $R^{10}$, $R^{11}$, $R^{12}$, and $R^{13}$ are H or ($C_1$–$C_6$)alkyl, and X and Y are each independently selected from H, halo, cyano, thiocyano, isothiocyano and ($C_1$–$C_6$) alkysulfonyloxy, provided that at least one of X and Y is not H.

In another embodiment of the method of the present invention, the compounds have the structural formula (I), wherein A is 3-pyridyl and the compounds have the structural formula:

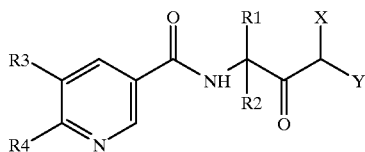

(IV)

wherein $R^1$ and $R^2$ are H, $(C_1-C_6)$alkyl, halo$(C_1-C_6)$alkyl, $(C_2-C_6)$alkenyl, and $(C_2-C_6)$alkynyl, provided that at least one of $R^1$ and $R^2$ is not H; $R^3$ and $R^4$, are each independently selected from H, halo, cyano, $(C_1-C_6)$alkyl, halo$(C_1-C_6)$alkyl, $(C_2-C_6)$alkenyl, $(C_2-C_6)$alkynyl, $(C_1-C_6)$alkoxyl, $(C_1-C_6)$alkylthio, halo$(C_1-C_6)$alkoxyl, nitro, carboxyl, —$NR^6R^7$, —$CR^8$=$NOR^9$, $NHCOOR_{10}$, —$CONR^{11}R^{12}$, and —$COOR^{13}$, $R^6$, $R^7$, $R^8$, $R^9$, $R^{10}$, $R^{11}$, $R^{12}$, and $R^{13}$ are H or $(C_1-C_6)$alkyl, and X and Y are each independently selected from H, halo, cyano, thiocyano, isothiocyano and $(C_1-C_6)$ alkysulfonyloxy, provided that at least one of X and Y is not H. $R^3$ and $R^4$ may together form a fused 5, 6 or 7 membered carbocyclic ring which may contain up to two heteroatoms selected from the group consisting of: O, S, N, and P.

In another embodiment of the method of the present invention, the compounds have the structural formula (1), A is 2-furyl or 2-thienyl and the compounds have the structural formula:

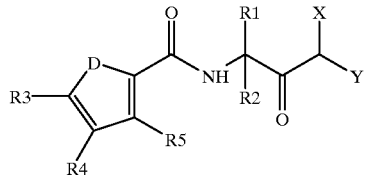

(V)

wherein:

D is O or S;

$R^1$ and $R^2$ are H, $(C_1-C_6)$alkyl, halo$(C_1-C_6)$alkyl, $(C_2-C_6)$alkenyl, and $(C_2-C_6)$alkynyl, provided that at least one of $R^1$ and $R^2$ is not H; $R^3$, $R^4$, and $R^5$ are each independently selected from H, halo, cyano, $(C_1-C_6)$alkyl, halo$(C_1-C_6)$alkyl, $(C_2-C_6)$alkenyl, $(C_2-C_6)$alkynyl, $(C_1-C_6)$alkoxyl, $(C_1-C_6)$alkylthio, halo$(C_1-C_6)$alkoxyl, nitro, carboxyl, —$NR^6R_7$, —$CR^8$=$NOR^9$, $NHCOOR^{10}$, —$CONR^{11}R^{12}$, and —$COOR^{13}$, $R^6$, $R^7$, $R^8$, $R^9$, $R^{10}$, $R^{11}$, $R^{12}$, and $R^{13}$ are H or $(C_1-C_6)$alkyl, and X and Y are each independently selected from H, halo, cyano, thiocyano, isothiocyano and $(C_1-C_6)$alkysulfonyloxy, provided that at least one of X and Y is not H. $R^3$ and $R^4$ may together form a fused 5, 6 or 7 membered carbocyclic ring which may contain up to two heteroatoms selected from the group consisting of: O, S, N, and P.

In another embodiment of the method of the present invention, using compounds having the structural formula (I), A is 3-furyl or 3-thienyl and the compounds have the structural formula:

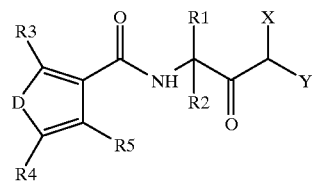

(VI)

wherein:

D is O or S;

$R^1$ and $R^2$ are H, $(C_1-C_6)$alkyl, halo$(C_1-C_6)$alkyl, $(C_2-C_6)$alkenyl, and $(C_2-C_6)$alkynyl, provided that at least one of $R^1$ and $R^2$ is not H; $R^3$, $R^4$, and $R^5$ are each independently selected from H, halo, cyano, $(C_1-C_6)$alkyl, halo$(C_1-C_6)$alkyl, $(C_2-C_6)$alkenyl, $(C_2-C_6)$alkynyl, $(C_1-C_6)$alkoxyl, $(C_1-C_6)$alkylthio, halo$(C_1-C_6)$alkoxyl, nitro, carboxyl, —$NR^6R^7$, —$CR^8$=$NOR^9$, $NHCOOR^{10}$, —$CONR^{11}R^{12}$, and —$COOR^{13}$, $R^6$, $R^7$, $R^8$, $R^9$, $R^{10}$, $R^{11}$, $R^{12}$, and $R^{13}$ are H or $(C_1-C_6)$alkyl, and X and Y are each independently selected from H, halo, cyano, thiocyano, isothiocyano and $(C_1-C_6)$alkysulfonyloxy, provided that at least one of X and Y is not H.

When $R^1$ and $R^2$ are different, optical enantiomers of the compounds of the present invention are possible due to the presence of an asymmetric carbon atom linking $R^1$ and $R^2$. It is known that many biologically active compounds have optical enantiomers, one of which is more active than the other. Similarly, for compounds used in the method of the present invention, the biological activity of one enantiomer may exceed that of the other enantiomer. In such cases, both enantiomers are within the scope of the present invention. For example, the "S enantiomers" of compounds 14 and 32 are more active than the corresponding "R enantiomers". The term "S enantiomer" means that the four groups on the carbon to which $R^1$ and $R^2$ are attached, when ranked according to the set of sequence rules of the Cahn-Ingold-Prelog system (*Angew. Chem. Int. Ed. Engl.* 5, 385–415 (1966)), define the carbon as having an S configuration. The term "R enantiomer" means that the four groups form an R configuration.

The method of the present invention utilizes the above-described compounds to control the growth of mammalian cells. In particular, the above-described compounds are useful in controlling the growth of cancer cells. While it is not intended that the invention be bound to any mechanistic theory, it is thought that the compounds used in the method of the present invention inhibit mitosis by interacting with tubulin. The compounds may be used to control cancer in mammals when taken up in a pharmaceutically acceptable carrier at a pharmacologically effective concentration. As used herein, the term "mammal" includes so-called warm-blooded animals such as dogs, rats, mice, cats, guinea pigs, horses, cattle, sheep, and primates including humans. As used herein, the term "controlling the growth" means slowing, arresting, interrupting, or stopping the growth and metastases of rapidly growing tissue, such as a tumor, in a mammal, it being understood that treatment does not generally provide a "cure" in the sense that the tissue is necessarily destroyed or totally eliminated.

Also within the scope of the present invention is a method for preventing cell reproduction by directly treating cells with one or more of the compounds described herein. More generally, the treatment of tumors and other diseases responsive to the inhibition of cell mitosis is within the scope of the method of the present invention. As used herein, the term "tumor" means both benign and malignant tumors or neoplasms and includes melanomas, lymphomas, leukemias and sarcomas. As used herein, the term "tumor" is to be construed as encompassing only those specific tumor tissues which are sensitive to treatment with compounds described herein.

Pharmaceutically acceptable acid addition salts of compounds described herein are also useful in treating disease. The term "pharmaceutically acceptable acid addition salts" is intended to include any non-toxic organic or inorganic acid addition salts of basic forms of the compounds described herein. In general, compounds having basic groups may form acid addition salts. When several basic groups are present, mono- or poly-salts may be formed. For example compounds such as those containing a pyridine ring or an amino substituent, may be reacted with a pharmaceutically acceptable acid, and the resulting acid addition salt may be administered. Suitable inorganic acids for use in preparing acid addition salts are well known to the art of pharmaceutical formulation and include hydrochloric, hydrobromic, hydroiodic, sulfuric, nitric, and phosphoric acids, and acid metal salts such as sodium monohydrogen orthophosphate and potassium hydrogen sulfate. Examples of organic acids which form suitable salts include mono, di, and tricarboxylic acids, such as acetic, glycolic, lactic, pyruvic, malonic, fumaric, benzoic, citric, maleic, tartaric, succinic, gluconic, ascorbic, sulfamic, oxalic, pamoic, hydroxymaleic, hydroxybenzoic, phenylacetic, salicylic, methanesulfonic, ethanesulfonic, 2-hydroxyethanesulfonic, benzenesulfonic, or 2-phenoxybenzoic acids or mixtures thereof. (See, for example Berge, et al., "Pharmaceutical Salts," in *J. Pharm. Sci.*, 66:1–19 (1977)). Acid addition salts may be prepared by standard techniques such as by dissolving the free base in aqueous or aqueous-alcohol solution or other suitable solvent containing the appropriate acid and isolating by evaporating the solution or by reacting the free base in an organic solvent in which case the salt separates directly or can be obtained by concentration of the solution. In general, acid addition salts are crystalline materials which are more soluble in water than the free base. As a specific example, the hydrochloride salt of compound 44 (described in Table 3, below) may be prepared by dissolving the compound in anhydrous ethyl ether, bubbling in dry hydrogen chloride gas, filtering, and drying the resultant precipitate.

For pharmaceutical use, the compounds described herein may be taken up in pharmaceutically acceptable carriers, such as, for example, solutions, suspensions, tablets, capsules, ointments, elixirs and injectable compositions. Pharmaceutical preparations may contain from 0.1% to 99% by weight of active ingredient. Preparations which are in single dose form, "unit dosage form", preferably contain from 20% to 90% active ingredient, and preparations which are not in single dose form preferably contain from 5% to 20% active ingredient. As used herein, the term "active ingredient" refers to compounds described herein, salts thereof, and mixtures of compounds described herein with other pharmaceutically active compounds. Dosage unit forms such as, for example, tablets or capsules, typically contain from about 0.05 to about 1.0 g of active ingredient. Pharmaceutical preparations may be adminstered orally, parenterally, or topically.

Pharmaceutical preparations containing compounds described herein may be prepared by methods known to those skilled in the art, such as, for example, conventional mixing, granulating, dissolving, or lyophilizing. Oral dosage forms include capsules, pills, tablets, troches, lozenges, melts, powders, solutions, suspensions and emulsions. For oral dosage forms, for example, the compounds may be combined with one or more solid pharmaceutically acceptable carriers, optionally granulating the resulting mixture. Pharmaceutically acceptable adjuvants may optionally be included, such as, for example, flow-regulating agents and lubricants. Suitable carriers include, for example, fillers such as sugars, cellulose preparations, calcium phosphates; and binders such as methylcellulose, hydroxymethylcellulose, and starches, such as, for example, maize starch, potato starch, rice starch, and wheat starch. Examples of orally administrable pharmaceutical preparations are dry-filled capsules consisting of gelatin, and soft sealed capsules consisting of gelatin and a plasticizer such as glycerol or sorbitol. The dry-filled capsules may contain the active ingredient in the form of a granulate, for example in admixture with fillers, binders, glidants, and stabilizers. In soft capsules, the active ingredient is preferably dissolved or suspended in a suitable liquid adjuvant, such as, for example, a fatty oil, paraffin oil, or liquid polyethylene glycol, optionally in the presence of stabilizers. Other oral adminstrable forms include syrups containing active ingredient, for example, in suspended form at a concentration of from about 5% to 20%, preferably about 10%, or in a similar concentration that provides a suitable single dose when administered, for example, in measures of 5 to 10 milliliters. Suitable excipients for use in oral liquid dosage forms include diluents such as water and alcohols, for example ethanol, benzyl alcohol and polyethylene alcohols, either with or without the addition of a pharmaceutically acceptable surfactant, suspending agent, or emulsifying agent. Also suitable are powdered or liquid concentrates for combining with liquids such as milk. Such concentrates may also be packed in single dose quantities.

Suitable rectally administrable pharmaceutical preparations include, for example, suppositories consisting of a combination of active ingredient with a suppository base material. Suitable suppository base materials include, for example, natural or synthetic triglycerides, paraffin hydrocarbons, polyethylene glycols, and alkanols.

The compounds described herein may be administered parenterally, that is, subcutaneously, intravenously, intramuscularly, or interperitoneally, as injectable dosages of the compound in a physiologically acceptable diluent with a pharmaceutical carrier. Solutions for parenteral administration may be in the form of infusion solutions. A pharmaceutical carrier may be, for example, a sterile liquid or mixture of liquids such as water, saline, aqueous dextrose and related sugar solutions, an alcohol such as ethanol, glycols such as propylene glycol or polyethylene glycol, glycerol ketals such as 2,2-dimethyl-1,3-dioxolane-4-methanol, ethers such as poly(ethyleneglycol)400, oils, fatty acids, fatty acid esters or glycerides, with or without the addition of a pharmaceutically acceptable surfactant such as a soap or detergent, suspending agent such as pectin, carbomers, methylcellulose, hydroxypropylmethylcellulose, or carboxymethylcellulose, or emulsifying agent or other pharmaceutically acceptable adjuvants. Examples of oils which may be used in parenteral formulations include petroleum, animal, vegetable, or synthetic oils such as, for example, peanut oil, soybean oil, sesame oil, cottonseed oil, corn oil, olive oil, petrolatum, and mineral oil. Suitable fatty acids include, for example, oleic acid, stearic acid, and isostearic acid. Suitable fatty acid esters include ethyl oleate and isopropyl myristate. Suitable soaps include alkaline metal, ammonium and triethanolamine salts of fatty acids. Suitable detergents include cationic detergents such as dimethyl dialkyl ammonium halides and alkyl pyridinium halides; anionic detergents such as alkyl, aryl and olefin sulfonates, monoglyceride sulfates and sulfosuccinates; nonionic detergents such as fatty amine oxides, fatty acid alkanolamides and polyoxyethylenepropylene copolymers; and amphoteric detergents such as alkyl-α-aminopropionates and 2-alkylimidazoline quaternary ammonium salts; as well as mixtures of detergents. Parenteral preparations will typically contain from about 0.5% to about 25% by weight of active ingredient in solution. Preservatives and buffers may also be used advantageously. Injection suspensions may include viscosity-increasing substances such as, for example, sodium carboxymethylcellulose, sorbitol or dextran, and may also include stabilizers. In order to minimize irritation at the site of injection, injectable compositions may contain a nonionic surfactant having a hydrophile-lipophile balance (HLB) of from about 12 to about 17. The quantity of surfactant in such formulations ranges from about 5% to about 15% by weight. The surfactant may be a single component having the above HLB or a mixture of two or more components having the desired HLB. Particular examples of useful surfactants include polyethylene sorbitan fatty acid esters, such as, for example, sorbitan monooleate.

It is generally known that therapeutic agents used in the treatment of disease such as cancer may be used in conjunction with other therapeutic agents or therapies known to be useful in treatment of the disease. In particular, the compounds described herein may be used in such conjunctive therapy. For example, the administration of a compound described herein may be used in conjunction with the excision of a tumor or with irradiation therapy, immunotherapy, or local heat therapy. Compounds described herein may advantageously be administered in conjunction with a chemical cytotoxic agent known to be useful for the treatment of tumors. It is known to those skilled in the art that combination therapy may provide enhanced therapeutic effects including slowing or prevention of regrowth of a tumor. It is also known to those skilled in the art that when using combination therapy, it is essential to avoid undesirable interactions between compounds or adverse effects on a patient due to inappropriate combinations of compounds. Combination therapy may also allow for smaller doses or fewer individual doses of cytotoxic agents to be used. Such combination therapy utilizing the compounds described herein is contemplated in the method of the present invention.

It will be understood that the amount of compound actually administered will be determined by a physician or veterinarian in the light of the relevant circumstances, including the condition to be treated and the chosen route of administration. At the discretion of a physician or veterinarian, the compounds may be administered therapeutically or prophylactically. Factors included in determining the dosage level include the nature and severity of the disease, the disease stage, and, when administered systemically, the age, sex, size and weight of the subject. The total amount of active ingredient administered will generally range from about 1 milligram (mg) per kilogram (kg) of subject weight to about 100 mg/kg, and preferably from about 3 mg/kg to about 25 mg/kg. A unit dosage may contain from about 25 mg to 1 gram of active ingredient, and may be administered one or more times per day.

The compounds may be applied topically to treat skin cancers. Skin cancers include, for example, cutaneous T-cell lymphoma, Sezany lymphoma, xeroderma pigmentosium, ataxia telangiectasia and Bloom's syndrome. A sufficient amount of a preparation containing a compound of the present invention is applied to cover a lesion or affected area. An effective concentration of active agent for topical application is generally within the range of from $10^{-3}$ moles/liter (M) to $10^{-5}$ M, preferably $10^{-4}$ M. The compounds may be taken up in a suitable carrier for topical application such as, for example, ointments, solutions and suspensions.

It will be understood by those skilled in the art that the compounds of the present invention may be useful in treating diseases, other than cancer, which may be inhibited by antimitotic agents. Treatment of such diseases may involve the use of a combination of pharmaceutical agents and the compounds used in the method of the present invention may be useful in such combination therapies. For example, treatment of gout typically involves the use of antiinflammatory drugs in combination with antimitotic agents such as colchicine, vinblastine and vincristine. The compounds of the present invention are also expected to be useful in the treatment of gout and may be used in conjunction with antiinflammatory drugs.

Particular compounds useful in the method of the present invention include those compounds listed in Tables 1–6.

Table 1 are shown compounds having the structural formula (II).

TABLE 1

| Compound | R1 | R2 | R3 | R4 | R5 | x | y |
|---|---|---|---|---|---|---|---|
| 1 | $CH_3$ | $C_2H_5$ | H | $NHCOOCH_3$ | H | Cl | H |
| 2 | $CH_3$ | $C_2H_5$ | Cl | $NH_2$ | Cl | Cl | H |
| 3 | $CH_3$ | $C_2H_5$ | CN | H | Cl | Cl | H |
| 4 | $CH_3$ | $C_2H_5$ | CH=NOCH$_3$ | H | Cl | Cl | H |
| 5 | $CH_3$ | $C_2H_5$ | Br | H | $CH_3$ | Cl | H |
| 6 | H | n-propyl | Cl | H | Cl | Br | Br |
| 7 | $CH_3$ | $C_2H_5$ | Br | H | H | Br | Br |
| 8 | $CH_3$ | isopropyl | Cl | H | Cl | Br | Br |
| 9 | $CH_3$ | isobutyl | Cl | H | Cl | Br | Br |
| 10 | $CH_3$ | n-pentyl | Cl | H | Cl | Br | Br |
| 11 | $CH_3$ | n-propyl | Cl | H | Cl | Br | Br |
| 12 | $C_2H_5$ | $C_2H_5$ | Cl | H | Cl | Br | Br |
| 13 | $CH_3$ | $C_2H_5$ | Cl | H | Cl | Br | Br |
| 14 | $CH_3$ | $C_2H_5$ | Cl | H | Cl | Cl | H |
| 15 | $CH_3$ | $CH_3$ | Cl | H | Cl | Br | Cl |
| 16 | $CH_3$ | $CH_3$ | H | H | H | Br | Br |
| 17 | $CH_3$ | $CH_3$ | Cl | H | Cl | Br | Br |

TABLE 1-continued

| Compound | R1 | R2 | R3 | R4 | R5 | x | y |
|---|---|---|---|---|---|---|---|
| 18 | $CH_3$ | $C_2H_5$ | CH=NOCH$_3$ | $NH_2$ | Cl | Cl | H |
| 19 | $CH_3$ | $C_2H_5$ | Br | $NH_2$ | Br | Cl | H |
| 20 | $CH_3$ | $C_2H_5$ | CN | H | H | Cl | H |
| 21 | $CH_3$ | $C_2H_5$ | Br | $CH_3$ | Br | Cl | H |
| 22 | $CH_3$ | $C_2H_5$ | NHCOOCH$_3$ | H | H | Cl | H |
| 23 | $CH_3$ | $C_2H_5$ | CN | H | $CH_3$ | Cl | H |
| 24 | $CH_3$ | $C_2H_5$ | CH=NOCH$_3$ | H | H | Cl | H |
| 25 | $CH_3$ | $C_2H_5$ | Cl | H | $CH_3$ | Cl | H |
| 26 | $CH_3$ | $C_2H_5$ | Cl | H | Cl | SCN | H |
| 27 | $CH_3$ | $CH_3$ | Cl | H | Cl | NCS | H |
| 28 | $CH_3$ | $CH_3$ | Cl | H | Cl | Cl | H |
| 29 | $CH_3$ | $CH_3$ | Cl | H | Cl | Br | H |
| 30 | $CH_3$ | $C_2H_5$ | Br | $CH_3$ | Cl | Cl | H |
| 31 | $CH_3$ | $C_2H_5$ | Cl | F | Cl | Cl | H |
| 32 | $CH_3$ | $C_2H_5$ | Cl | $CH_3$ | Cl | Cl | H |
| 33 | $CH_3$ | $C_2H_5$ | Cl | Cl | Cl | Cl | H |
| 34 | $CH_3$ | $C_2H_5$ | F | H | F | Cl | H |
| 35 | $CH_3$ | $C_2H_5$ | Cl | H | H | Cl | H |
| 36 | $CH_3$ | $C_2H_5$ | H | H | H | Cl | H |
| 37 | $CH_3$ | $C_2H_5$ | F | F | F | Cl | H |
| 38 | $CH_3$ | isopropyl | Cl | H | Cl | Cl | H |
| 39 | $CH_3$ | $CH_3$ | H | H | H | Cl | H |
| 40 | $CH_3$ | $CH_3$ | Cl | H | Cl | Cl | Cl |
| 41 | $CH_3$ | $C_2H_5$ | Cl | H | Br | Br | Br |

Table 2 lists compounds having the structural formula (III).

TABLE 2

| Compound | R1 | R2 | R3 | R5 | x | y |
|---|---|---|---|---|---|---|
| 42 | $CH_3$ | $CH_3$ | Cl | Cl | Br | Br |
| 43 | $CH_3$ | $CH_3$ | Cl | Cl | Cl | H |

Table 3 lists compounds having the structural formula (IV).

TABLE 3

| Compound | R1 | R2 | R3 | R4 | x | y |
|---|---|---|---|---|---|---|
| 44 | $CH_3$ | $C_2H_5$ | Br | H | Cl | H |
| 45 | $CH_3$ | $C_2H_5$ | H | H | Cl | H |
| 46 | $CH_3$ | $C_2H_5$ | H | Cl | Cl | H |

Table 4 lists compounds having the structural formula (V)

TABLE 4

| Compound | D | R1 | R2 | R3 | R4 | R5 | x | y |
|---|---|---|---|---|---|---|---|---|
| 47 | S | $CH_3$ | $CH_3$ | Br | Br | H | Cl | H |
| 48 | S | $CH_3$ | $C_2H_5$ | $CH_3$ | H | H | Cl | H |
| 49 | S | $CH_3$ | $CH_3$ | H | H | H | Br | Br |
| 50 | O | $CH_3$ | $C_2H_5$ | Br | H | H | Br | Br |
| 51 | S | $CH_3$ | $CH_3$ | H | H | H | Cl | H |

Table 5 lists compounds having the structural formula (VI).

TABLE 5

| Compound | D | R1 | R2 | R3 | R4 | R5 | x | y |
|---|---|---|---|---|---|---|---|---|
| 52 | S | $CH_3$ | $CH_3$ | Cl | Cl | H | Cl | H |

Table 6 lists compounds having the structural formula (II), wherein $R^4$ and $R^5$ together form a fused ring.

TABLE 6

| Compound | R1 | R2 | R3 | R4R5 | x | y |
|---|---|---|---|---|---|---|
| 53 | $CH_3$ | $C_2H_5$ | H | —N=CH—O— | Cl | H |
| 54 | $CH_3$ | $C_2H_5$ | H | —O—CH=N— | Cl | H |
| 55 | $CH_3$ | $C_2H_5$ | H | —N=CH—S— | Cl | H |
| 56 | $CH_3$ | $C_2H_5$ | Cl | —N=CH—O— | Cl | H |
| 57 | $CH_3$ | $C_2H_5$ | Cl | —N=C(CH$_3$)—O— | Cl | H |

Table 7 lists compounds having the structural formula (I).

TABLE 7

| Compound | A | R1 | R2 | x | y | z |
|---|---|---|---|---|---|---|
| 58 | cyclohexyl | $CH_3$ | $CH_3$ | Cl | H | H |
| 59 | C(Cl)$_3$ | $CH_3$ | $CH_3$ | Cl | H | H |
| 60 | C(Cl)$_3$ | $CH_3$ | $CH_3$ | Br | Br | H |

Methods used in preparing compounds listed in Tables 1–7

Compounds 3, 5, 6, 7 8, 9, 10, 11, 12, 13, 14, 15, 16, 17, 20, 23, 25, 26, 27, 28, 29, 31, 33, 34, 35, 36, 37, 38, 39, 40 and 41 in Table 1:

Compounds 3, 5, 6, 7, 8, 9, 10, 11, 12, 13, 14, 15, 16, 17, 20, 23, 25, 26, 27, 28, 29, 31, 33, 34, 35, 36, 37, 38, 39, 40 and 41 in Table 1 were prepared according to synthetic methods described in U.S. Pat. No. 4,822,902, columns 5–8 and 11–17.

Compounds 4 and 24 in Table 1:

Compounds 4 and 24 in Table 1 were prepared according to synthetic methods described in U.S. Pat. No. 5,254,584, columns 7 and 8 (compound 24) and 10–14 (compound 4).

Compounds 21, 30 and 32 in Table 1:

Compounds 21, 30 and 32 were prepared according to synthetic methods described in U.S. Pat. No. 5,304,572, columns 4–8.

Compounds 2 and 19 in Table 1:

Compounds 2 and 19 were prepared using conventional synthesis techniques, as described for example in U.S. Pat. No. 4,863,940, columns 5–7, from appropriate benzoic acids or benzoyl chlorides. Thus, compounds 2 and 19 were prepared using 4-amino-3,5-dibromobenzoylchloride and 4-amino-3,5-dichlorobenzoylchloride, respectively.

Compound 18 in Table 1:

Compound 18 was prepared by reaction of the benzoyl chloride VII, in which $R^3$ is Cl, $R^4$ is $NH_2$ and $R^5$ is $CHNOCH_3$, with the α-amino-α'-chloroketone derivative VIII, in which R1 is methyl and R2 is ethyl, as illustrated in Scheme A:

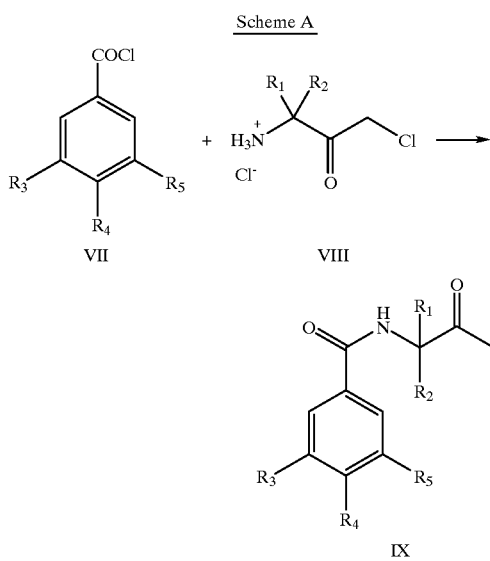

The starting benzoyl chloride used to prepare compound 18 can be prepared as indicated below in scheme B.

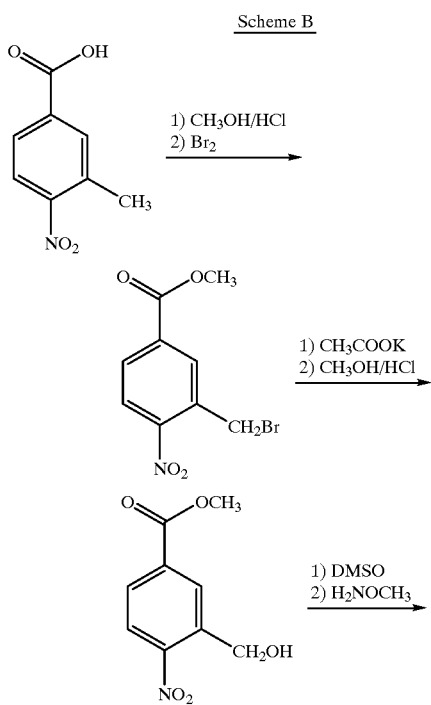

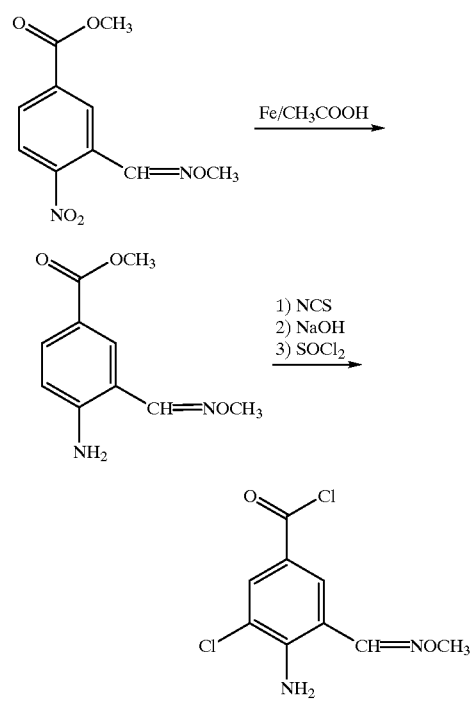

Compound VIII can be prepared by treating the acetylenic amine (X) with trifluoracetic anhydride in the presence of a solvent such as methylene chloride, chloroform, ethyl ether, or water and a base such as triethylamine, sodium carbonate, sodium bicarbonate, or sodium hydroxide to yield the acetylenic amide XI:

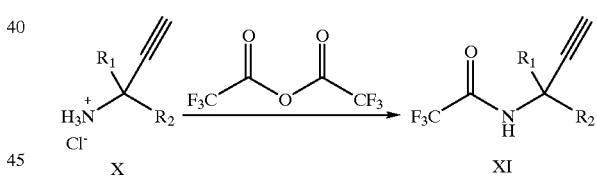

Treatment of the acetylenic amide XI with chlorine or a chlorine source at a temperature of from −78° C. to 0° C. in the presence of a solvent such as methylene chloride or chloroform yields the intermediate oxazoline (XII). The oxazoline XII may be readily hydrolyzed under acidic conditions using an acid such as hydrochloric acid or sulfuric acid with a solvent such as methanol or tetrahydrofuran at a temperature of from 40° C. to 60° C., yielding the α-amino-α', α'-dichloroketone (XIII).

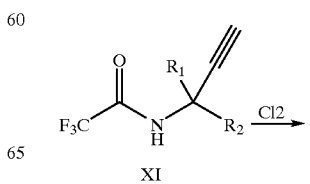

-continued

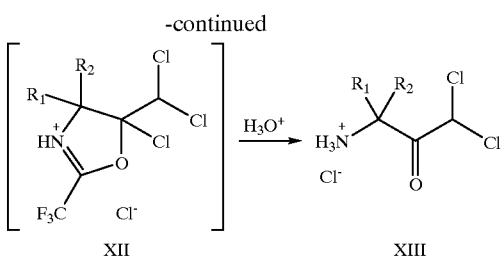

Selective catalytic dehalogenation of XIII yields the respective α-amino-α'-chloroketone derivative VIII:

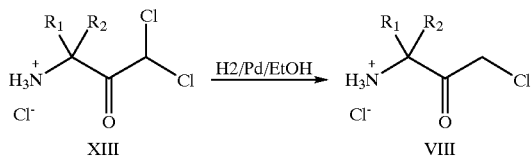

a) Preparation of methyl 3-methyl-4-nitrobenzoate

In a 5-liter three-necked round-bottomed flask equipped with a reflux condenser, overhead stirrer and gas inlet, was placed 300 g of 3-methyl-4-nitrobenzoic acid and 3 l of methanol. To the resulting well-stirred solution was bubbled in 20.8 g of hydrogen chloride and the resulting mixture was refluxed for 3 hours. The reaction mixture was cooled to room temperature and allowed to stand overnight. The expected methyl 3-methyl-4-nitrobenzoate precipitated as light yellow crystals, which were collected by suction filtration yielding after drying 259.3 g. This solid was used as such in the next step.

b) Preparation of methyl 3-bromomethyl-4-nitrobenzoate

In a 5-liter three-necked round-bottomed flask equipped with a reflux condenser, overhead stirrer, addition funnel and nitrogen inlet, was placed 220 g of methyl 3-methyl-4-nitrobenzoate, 2 l of anhydrous carbon tetrachloride and 4 g of benzoyl peroxide. To the resulting solution, irradiated with a 275 watt UV light, was added 198 g of bromine dropwise over a period of 2 hours at reflux. After the addition was complete the reaction mixture was refluxed for an additional 60 hours. The reaction mixture was cooled to room temperature. The solid which formed was separated by suction filtration. This solid (159.1 g) consisted of the expected methyl 3-bromomethyl-4-nitrobenzoate with minor amounts of the starting material. The mother liquors together with another 220 g of methyl 3-methyl-4-nitrobenzoate and 4 g of benzoyl peroxide were returned to the flask and treated with 198 g of bromine as described above. After the addition was complete the reaction mixture was refluxed another 96 hours, cooled to room temperature and the resulting solid separated by filtration yielding another 252 g of methyl 3-bromomethyl-4-nitrobenzoate. The solids were combined yielding a total of 411.1 g of methyl 3-bromomethyl-4-nitrobenzoate with minor amounts of the starting methyl 3-methyl-4-nitrobenzoate and methyl 3-dibromomethyl-4-nitrobenzoate. This solid was used as such in the next step.

c) Preparation of methyl 3-acetoxymethyl-4-nitrobenzoate

In a 5-liter three-necked round-bottomed flask equipped with a reflux condenser, overhead stirrer and nitrogen inlet, was placed 411 g of the previously prepared methyl 3-bromomethyl-4-nitrobenzoate, 441 g of anhydrous potassium acetate and 2 l of glacial acetic acid. The resulting mixture was refluxed for 4 hours, cooled to room temperature and stirred overnight. The solvent was removed in a rotary evaporator and the resulting light yellow solid treated with a mixture of 2 l of ethyl acetate and 1 l of water. The organic phase was separated, washed with water (3×400 mL), brine (1×400 mL) dried over anhydrous magnesium sulfate and the solvent removed using a rotary evaporator. The crude reaction mixture was triturated with hexane and filtered yielding 318 g of the expected methyl 3-acetoxymethyl-4-nitrobenzoate. This compound was used as such in the next step.

d) Preparation of methyl 3-hydroxymethyl-4-nitrobenzoate

In a 5-liter three-necked round-bottomed flask equipped with a reflux condenser, overhead stirrer and nitrogen inlet, was placed 318 g of the previously prepared methyl 3-acetoxymethyl-4-nitrobenzoate and 3.2 l of anhydrous methanol. To the resulting solution was bubbled in 40 g of hydrogen chloride and the resulting mixture was refluxed for 3 hours. After cooling to room temperature the solvent was removed using a rotary evaporator yielding 273 g of methyl 3-hydroxymethyl-4-nitrobenzoate as a yellow solid containing traces of methanol, which was used as such in the next step.

e) Preparation of methyl 3-formyl-4-nitrobenzoate

In a 5-liter four-necked round-bottomed flask 1.5 l of methylene chloride was cooled to −78° C. Oxalyl chloride (164 g, 1.29 moles) was added slowly, followed by dropwise addition of 202 g (2.59 moles) of dry dimethylsulfoxide in 125 mL of methylene chloride, keeping the temperature below −70° C. After the addition was complete the reaction mixture was stirred at −78° C. for 30 minutes and 273 g (1.29 moles) of previously prepared methyl 3-hydroxymethyl-4-nitrobenzoate dissolved in 250 mL of methylene chloride was added dropwise. The reaction mixture was stirred an additional 30 minutes. Triethylamine (392 g 3.88 moles) in 125 mL of methylene chloride was added dropwise keeping the temperature below −65° C. The reaction mixture was warmed up slowly to room temperature and stirred overnight. The solvent was removed using a rotary evaporator and the resulting solid treated with a mixture of 2 l of ethyl acetate and 1 l of water. The organic phase was separated, filtered through diatomaceous earth, and washed sequentially with dilute aqueous hydrochloric acid (2×250 mL), water (2×250 mL), saturated aqueous sodium bicarbonate (2×250 mL), water (2×200 mL), brine (200 mL) and dried over anhydrous magnesium sulfate. The solvent was removed using a rotary evaporator. The crude reaction mixture was triturated with hexane and filtered yielding 234.1 g of the expected methyl 3-formyl-4-nitrobenzoate as a yellow solid. This compound was used as such in the next step.

f) Preparation of methyl 3-methoxyiminomethyl-4-nitrobenzoate

To a well stirred mixture of 195 g of methyl 3-formyl-4-nitrobenzoate, 1 l methylene chloride and 370 mL of water was added sequentially 77.6 g of methoxylamine hydrochloride, 76.2 g of sodium acetate and 6.8 g of tetra-n-butylammonium hydrogen sulfate. The resulting mixture was stirred overnight at room temperature, then diluted with 2 l of ethyl ether. The organic phase was separated and washed sequentially with water (1×500 mL), 2% aqueous hydrochloric acid (2×500 mL), water (2×250 mL), and brine (1×250 mL); then dried over anhydrous magnesium sulfate. The solvent was removed using a rotary evaporator yielding 218.6 g of the expected methyl 3-methoxyiminomethyl-4-nitrobenzoate as a reddish oil that solidified upon standing, and which was used as such in the next step.

g) Preparation of methyl 4-amino-3-methoxyiminomethylbenzoate

In a 5-liter three-necked round-bottomed flask was placed 0.9 l of 5% aqueous acetic acid and 157 g (2.8 moles) of iron. To the resulting well-stirred mixture was added 166.6 g (0.7 moles) of the previously prepared methyl 3-methoxyiminomethyl-4-nitrobenzoate dissolved in 0.9 l of ethyl acetate followed by dropwise addition of 0.9 l of acetic acid while keeping the temperature below 35° C. The resulting mixture was stirred at 35° C. for 30 minutes and filtered through diatomaceous earth. The filtrate was poured into 5 l of water. The aqueous phase was separated and washed with ethyl ether (2×500 mL). The combined organic layers were washed sequentially with water (4×500 mL), saturated aqueous sodium bicarbonate (2×500 mL), water (2×500 mL), and brine (1×400 mL). The organic layer was dried over anhydrous magnesium sulfate and the solvent removed using a rotary evaporator yielding 130 g of the expected methyl 4-amino-3-methoxyiminomethylbenzoate.

h) Preparation of methyl 4-amino-3-chloro-5-methoxyiminomethylbenzoate

In a 2-liter three-necked round-bottomed flask was placed 106 g (0.51 moles) of the previously prepared 4-amino-3-methoxyiminomethylbenzoate and 500 mL of acetonitrile. The resulting mixture was heated at 70° C. and 75.2 g (0.56 moles) of N-chlorosuccinimide was added portionwise while keeping the temperature below 80° C. After the addition was complete the reaction mixture was refluxed for 1 hour. The reaction mixture was cooled to room temperature and the solvent eliminated in a rotary evaporator. The crude product was dissolved in 5 l of ethyl acetate. The organic solution was washed with water (3×500 mL) and then brine, dried over magnesium sulfate. The reaction mixture was concentrated in a rotary evaporator to a slurry, triturated with hexane and filtered yielding the expected methyl 4-amino-3-chloro-5-methoxyiminomethylbenzoate as a yellow solid. This reaction was repeated using the same amounts yielding a total of 210.5 g of methyl 4-amino-3-chloro-5-methoxyiminomethylbenzoate, which was used as such in the next step.

i) Preparation of 4-amino-3-chloro-5-methoxyiminomethylbenzoic acid

In a 5-liter three-necked round-bottomed flask was placed 210 g (0.86 moles) of the previously prepared 4-amino-3-chloro-5-methoxyiminomethylbenzoate, 1.7 l of methanol and 462 g (1.73 moles) of 15% aqueous sodium hydroxide. The resulting mixture was refluxed for 3 hours, after which the reaction mixture was stirred overnight at room temperature. The reaction mixture was concentrated using a rotary evaporator. The crude reaction mixture was dissolved in 2 l of water. The resulting aqueous solution was washed once with 500 mL of ethyl acetate, cooled in an ice bath and acidified to pH=2 with concentrated hydrochloric acid. The expected 4-amino-3-chloro-5-methoxyiminomethylbenizoic acid precipitated as a light yellow solid which was separated by suction filtration. The filter cake was washed with a 1:2 mixture of ethyl ether and hexane yielding after drying 185.2 g (94% yield).

j) Preparation of 4-amino-3-chloro-5-methoxyiminomethylbenzoyl chloride

In a 5-liter three-necked round-bottomed flask was placed 180 g of the previously prepared 4-amino-3-chloro-5-methoxyiminomethylbenzoic acid, 2 l of toluene, 3 mL of dimethylformamide and 104 g (64 mL) of thionyl chloride. The resulting mixture was heated at 70° C. for 2 hours, filtered while hot and the solvent removed using a rotary evaporator yielding 178.1 g of the expected 4-amino-3-chloro-5-methoxyiminomethylbenzoyl chloride.

k) Preparation of 3-amino-1-chloro-3-methyl-2-pentanone hydrochloride (Compound VIII, wherein $R^1$ is methyl and $R^2$ is ethyl)

i) Preparation of N-[3-(3-methyl-1-pentynyl)]trifluoroacetamide

In a 3 liter, four-necked, round-bottomed flask fitted with a mechanical stirrer, nitrogen inlet and thermometer was placed 234 grams (g) (1.75 mole) of 3-amino-3-methyl-1-pentyne hydrochloride and 1,000 mL of methylene chloride. To the resulting well-stirred mixture was added slowly 354 g (3.51 mole) of triethylamine (TEA) dropwise, keeping the temperature below 30° C. After the addition was completed, the reaction mixture was stirred 120 minutes followed by dropwise addition of 334.5 g (1.59 mole) of trifluoroacetic anhydride dissolved in 500 mL of methylene chloride at such a rate to keep the reaction temperature at 0° C. After the addition was completed the reaction mixture was stirred at room temperature overnight and concentrated in vacuo. The resulting slurry was washed with ethyl ether. The ethyl ether layer was washed sequentially with water, saturated aqueous sodium bicarbonate and brine, dried over anhydrous magnesium sulfate, treated with activated charcoal, and filtered through Celite™. The solvent was eliminated under reduced pressure. The resulting crude product was treated with cold pentane, filtered, and dried yielding 255.5 g (83%) of the expected N-[3-(3-methyl-1-pentynyl)]trifluoroacetamide as a white solid.

ii) Preparation of 5-chloro-5-(dichloromethyl)-4-ethyl-4-methyl-2-trifluoromethyloxazoline hydrochloride In a 5 L, four-necked, round-bottomed flask fitted with a mechanical stirrer, a thermometer, and a gas inlet was dissolved 255.5 g (1.32 mole) of N-[3-(3-methyl-1-pentynyl)]trifluoroacetamide in 4,000 mL of methylene chloride. The resulting mixture was cooled to −30° C. and 235 g of chlorine was bubbled in over a 2 hour period. When the addition was completed the reaction mixture was stirred at −30° C. during 30 minutes and warmed to room temperature. The crude reaction mixture was evaporated in the rotary evaporator yielding the expected 5-chloro-5-(dichloromethyl)-4-ethyl-4-methyl-2-trifluoromethyloxazoline hydrochloride which was used as such in the next step.

iii) Preparation of 3-amino-1,1-dichloro-3-methyl-2-pentanone hydrochloride

The 5-chloro-5-(dichloromethyl)-4-ethyl-4-methyl-2-trifluoromethyloxazoline hydrochloride prepared in the preceding step was dissolved in 1800 mL of methanol, 72 mL of water, and 190 mL of concentrated hydrochloric acid, warmed to 50° C., and stirred at that temperature overnight. The crude reaction mixture was cooled and poured into an ice/water/ethyl ether mixture. The phases were separated and the ether layer was extracted once with water. The ether was saved (organic I). The combined aqueous layers were washed once with ethyl ether, and the organic layer was combined with organic I (organic II). The aqueous layer was neutralized with saturated aqueous sodium bicarbonate and extracted twice with ethyl ether. The combined ether layers were washed with water, brine, dried over anhydrous magnesium sulfate, treated with activated charcoal, and filtered through Celite™. To the resulting colorless solution was bubbled in anhydrous hydrogen chloride keeping the temperature below 20° C. The resulting white solid was filtered and dried yielding 124.8 g of the expected 3-amino-1,1-dichloro-3-methyl-2-pentanone hydrochloride as a white solid. The ethyl ether filtrate was combined with organic II and concentrated in vacuo; the resulting residue (150 g) was taken in a mixture of methanol/water/concentrated hydrochloric acid and heated at 50° C. over the weekend. The previously described workup yielded another 51 g of 3-amino-1,1-dichloro-3-methyl-2-pentanone hydrochloride. The total amount obtained was 175.8 g (61% yield).

iv) Preparation of 3-amino-1-chloro-3-methyl-2-pentanone hydrochloride

In a 2 L Parr™ bottle was placed 41 g of 3-amino-1,1-dichloro-3-methyl-2-pentanone hydrochloride, 0.8 g of 10% palladium over charcoal, and 400 mL of ethanol. The resulting mixture was shaken in a Parr™ apparatus at 50 psi for 3 hours. The crude reaction mixture was filtered through Celite™ and evaporated in vacuo yielding a viscous oil, which was taken in 300 to 400 mL of ethyl acetate and stirred at room temperature for several hours. The expected 3-amino-1-chloro-3-methyl-2-pentanone hydrochloride crystallized as a white solid; 300 mL of hexane was added to the resulting suspension and filtered yielding 34 g (98%) of the expected 3-amino-1-chloro-3-methyl-2-pentanone hydrochloride.

The reaction was repeated starting with 41 g; 41 g; and 51 g of 3-amino-1,1-dichloro-3-methyl-2-pentanone hydrochloride yielding a total of 132.1 g (90% overall yield) of 3-amino-1-chloro-3-methyl-1-pentanone hydrochloride.

1) Preparation of 4-amino-3-chloro-5-methoxyiminomethyl-N-(3-chloro-1-ethyl-1-methyl-2-oxopropyl)benzamide (compound 18)

In a 5-liter three-necked round bottomed flask was placed 93 g of 3-amino-1-chloro-3-methyl-2-pentanone hydrochloride and 885 mL of water. To the resulting solution were added 138.6 g of sodium bicarbonate followed by 500 mL of ethyl acetate. To the resulting well-stirred mixture was added 123.5 g of 4-amino-3-chloro-5-methoxyiminomethylbenzoyl chloride dissolved in 1000 mL of ethyl acetate at room temperature over a period of 50 minutes. After the addition was complete the reaction mixture was stirred at room temperature for 1 hour. The two phases were separated and the organic layer was washed with water (2×500 mL), brine (1×500 mL), dried over anhydrous magnesium sulfate and the solvent eliminated in a rotary evaporator yielding the crude product as a brown oil. This oil was passed through a short silica gel column using methylene chloride as elution solvent. Evaporation of the solvent yielded 133.3 g of the expected 4-amino-3-chloro-5-methoxyiminomethyl-N-(3-chloro-1-ethyl-1-methyl-2-oxopropyl)benzamide as an off-white solid (mp 140–141° C.).

Compounds 1 and 22 in Table 1:

Compound 22 was prepared by the following procedure.

3-Nitro-N-(3-chloro-1-ethyl-1-methyl-2-oxopropyl)benzamide was prepared by reaction of 3-nitrobenzoylchloride with VIII as in scheme A (above), then converted to 3-amino-N-(3-chloro-1-ethyl-1-methyl-2-oxopropyl)benzamide by catalytic hydrogenation using palladium as the catalyst.

In a 300 ml, 4-necked, round-bottomed flask fitted with a mechanical stirrer, a thermometer and addition funnel was suspended 3.5 g of 3-amino-N-(3-chloro-1-ethyl-1-methyl-2-oxopropyl)benzamide in 100 ml of dichloromethane. The mixture was cooled to 0–5° C. in an ice bath, then 1.8 ml of triethylamine was added and the mixture allowed to stir for a few minutes. Methylchloroformate (1.1 ml) was added slowly, dropwise keeping the temperature under 5° C., and the mixture stirred for 20 minutes. The ice bath was removed and the reaction mixture allowed to warm to room temperature. The reaction mixture was washed twice with 50 ml of water and dried over anhydrous magnesium sulfate. The solvent was removed using a rotary evaporator, yielding the crude product. The crude product was purified by chromatography on silica gel, yielding 230 mg of compound 22.

Compound 1 was prepared by the same procedure as compound 22, but using 4-nitrobenzoylchloride as the starting material.

Compounds in Tables 2, 3, 4, 5 and 7:

Compounds in Tables 2, 3, 4, 5 and 7 were prepared according to synthetic methods described in U.S. Pat. No. 4,863,940.

Compounds 53, 54, 56 and 57, In Table 6:

Compounds 53, 54, 56 and 57 were prepared by reaction of the corresponding aromatic derivative (VII), in which $R_4$ and $R_5$ together form a fused ring, with 3-amino-1-chloro-3-methyl-2-pentanone hydrochloride (compound VIII in which $R_1$ is methyl and $R_2$ is ethyl) as illustrated above in Scheme A:

To prepare compound 55, 6-carboxy-1,3-benzothiazole (purchased from Maybridge Chemical Company Ltd.) was first treated with thionyl chloride to give the acid chloride. The acid chloride was treated with 3-amino-1-chloro-3-methyl-2-pentanone hydrochloride in the presence of triethylamine to yield compound 55.

To prepare the aromatic portion of compound 54, the 5-carboxy benzoxazole derivative XIV was prepared from the corresponding 2-amino phenol derivative by procedures known in the art and described in, for example, E. C. Taylor, ed., *The Chemistry of Heterocyclic Compounds*, vol. 47, John Wiley & Sons, 1987 "Synthesis of Fused Heterocycles", edited by G. P. Ellis; p. 50, part I and pp. 713–714 part II). This procedure is set forth below:

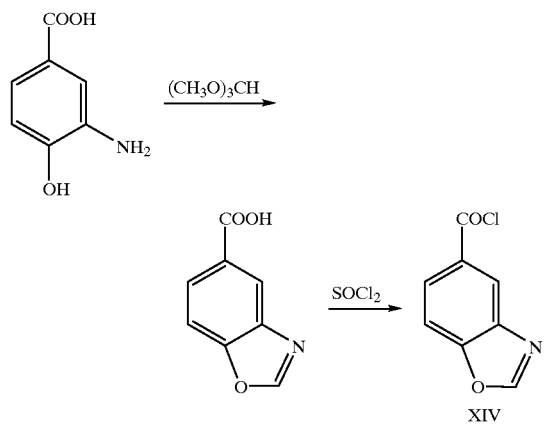

XIV was then treated with 3-amino-1-chloro-3-methyl-2-pentanone hydrochloride in the presence of triethylamine to yield compound 54.

To prepare the aromatic portions of compounds 53, 56 and 57, the 6-carboxy benzoxazole derivatives (XV) were prepared from the corresponding 2-amino phenol derivatives by the procedure set forth below:

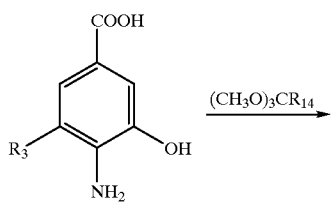

-continued

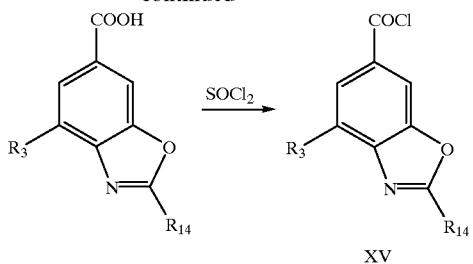

wherein R14 is H or CH3

To prepare compound 53, 6-carboxy-1,3-benzoxazole was prepared from 4-amino-3-hydroxy benzoic acid by treatment with trimethylorthoformate. 6-Carboxy-1,3-benzoxazole was first treated with thionyl chloride to give the acid chloride. The acid chloride was treated with 3-amino-1-chloro-3-methyl-2-pentanone hydrochloride in the presence of triethylamine to yield compound 53.

To prepare compound 56, 6-carboxy-4-chloro-1,3-benzoxazole was prepared from 4-amino-5-chloro-3-hydroxy benzoic acid by treatment with trimethylorthoformate. 6-carboxy-4-chloro-1,3-benzoxazole was first treated with thionyl chloride to give the acid chloride. The acid chloride was treated with 3-amino-1-chloro-3-methyl-2-pentanone hydrochloride in the presence of triethylamine to yield compound 56.

To prepare compound 57, 6-carboxy-2-methyl-4-chloro-1,3-benzoxazole was prepared from 4-amino-5-chloro-3-hydroxy benzoic acid by treatment with trimethylorthoacetate. 6-carboxy-2-methyl-4-chloro-1,3-benzoxazole was first treated with thionyl chloride to give the acid chloride. The acid chloride was treated with 3-amino-1-chloro-3-methyl-2-pentanone hydrochloride in the presence of triethylamine to yield compound 57.

EXAMPLES

The following examples are provided in order to illustrate the method of the present invention.

Example 1

Growth Inhibition of Mouse Lymphoma Cells

Effects of compounds on growth of mouse lymphoma cell line L5178Y, were determined as follows. Cells were grown in Fischer's medium (obtained from Life Technologies, Inc., Gaithersburg, Md.) containing 0.24 grams per liter (g/l) sodium pyruvate, 1.12 g/l surfactant (Pluronic F-68, from BASF Corporation, Parsippany, N.J.), and 10% by volume (10% v/v) heat-inactivated horse serum (obtained from Life Technologies, Inc) at 37° C. To 30 ml aliquots of cell suspension ($2 \times 10^4$ cells per milliliter (mL)) in exponential growth phase were added test compounds dissolved in dimethylsulfoxide (DMSO) at various concentrations such that the final DMSO concentration in the mixtures was 0.25%. Tubes were gassed with 5% $CO_2$ then incubated on a roller drum apparatus. After 48 hours the cells were treated with 0.1% trypsin (Life Technologies, Inc.,) for 10 minutes and counted in a Coulter Counter equipped with a 140 micrometer ($\mu$M) aperture. Percent inhibition of growth was calculated by comparing the number of cells in assays containing test compound with the number of cells in controls lacking the test compound. Results are shown in Table 8.

TABLE 8

Growth inhibition of mouse lymphoma cells by N-acetonylarylamides

| Compound | Concentration (micromolar) | Inhibition of growth (%) |
|---|---|---|
| 1 | 2 | 92 |
| 2 | 2 | 91 |
| 3 | 2 | 94 |
| 44 | 2 | 95 |
| 4 | 2 | 95 |
| 5 | 2 | 91 |
| 6 | 2 | 75 |
| 7 | 2 | 92 |
| 8 | 2 | 83 |
| 42 | 2 | 98 |
| 9 | 2 | 97 |
| 10 | 2 | 96 |
| 11 | 2 | 88 |
| 49 | 2 | 97 |
| 12 | 2 | 85 |
| 13 | 2 | 98 |
| 14 | 2 | 95 |
| 15 | 2 | 90 |
| 16 | 2 | 98 |
| 17 | 2 | 97 |
| 60 | 2 | 98 |
| 18 | 2 | 94 |
| 19 | 4 | 97 |
| 20 | 4 | 96 |
| 21 | 4 | 97 |
| 43 | 4 | 92 |
| 59 | 4 | 91 |
| 22 | 10 | 96 |
| 55 | 10 | 97 |
| 23 | 10 | 95 |
| 24 | 10 | 96 |
| 25 | 10 | 95 |
| 50 | 10 | 95 |
| 26 | 10 | 67 |
| 27 | 10 | 61 |
| 28 | 10 | 87 |
| 29 | 10 | 95 |
| 56 | 10 | 81 |
| 57 | 10 | 97 |
| 30 | 20 | 97 |
| 31 | 20 | 97 |
| 32 | 20 | 96 |
| 52 | 20 | 89 |
| 33 | 20 | 94 |
| 34 | 20 | 88 |
| 35 | 20 | 95 |
| 47 | 20 | 96 |
| 53 | 50 | 95 |
| 36 | 50 | 91 |
| 54 | 50 | 36 |
| 37 | 50 | 96 |
| 46 | 50 | 84 |
| 45 | 50 | 36 |
| 48 | 50 | 97 |
| 38 | 50 | 66 |
| 51 | 50 | 95 |
| 39 | 50 | 96 |
| 40 | 50 | 92 |
| 58 | 50 | 77 |

Example 2

Growth Inhibition of Human Tumor Cell Lines

Selected compounds were evaluated by the National Cancer Institute, Bethesda, Md. against 60 human tumor cell lines according to procedures described in *Principles and Practices of Oncology*, volume 3, issue number 10, pp. 1–12. Results of the testing against representative cell lines including the test compound number, and the $GI_{50}$ values ($\mu$M) are set forth in Table 3. The $GI_{50}$ value is the concentration required to inhibit cell growth by 50% as compared to untreated control cultures.

TABLE 9

Growth inhibition of human tumor cell lines

| Compound | GI$_{50}$ ($\mu$M) Cell Line | | | | | | | |
|---|---|---|---|---|---|---|---|---|
| | A | B | C | D | E | F | G | H |
| 4 | 0.59 | 2.14 | 1.54 | 2.58 | 2.31 | 3.24 | 2.62 | 3.07 |
| 7 | 2.32 | 1.08 | 1.83 | 3.39 | 2.29 | 2.74 | 3.01 | 2.82 |
| 13 | 0.28 | 0.28 | 0.24 | 1.39 | 1.90 | 2.08 | 1.82 | 1.92 |
| 14 | 0.83 | 1.98 | 0.72 | 2.31 | 2.10 | 1.94 | 2.79 | 3.83 |
| 15 | 2.85 | 1.29 | 6.65 | 10.40 | 10.80 | 16.60 | 12.10 | 10.80 |
| 17 | 1.79 | 1.04 | 2.09 | 3.65 | 2.25 | 2.71 | 3.00 | 2.37 |
| 23 | 0.65 | 2.05 | 2.19 | 3.28 | 2.55 | 2.56 | 3.43 | 2.81 |
| 26 | 5.69 | 3.77 | 3.71 | 4.85 | 3.45 | 12.20 | 11.90 | 13.30 |
| 28 | 3.01 | 2.61 | 5.38 | 14.20 | 9.79 | 12.20 | 12.40 | 12.90 |
| 44 | 0.33 | 0.35 | 0.33 | 0.67 | 2.21 | 0.41 | 1.96 | 2.36 |

A = Leukemia (SR)
B = Non-small cell lung cancer (NCI-H522)
C = Small cell lung cancer (DMS 114)
D = Colon cancer (HCT-116)
E = CNS cancer (SF-539)
F = Melanoma (SK-MEL-2)
G = Ovarian cancer (OVCAR-8)
H = Renal cancer (CAKI-1)

Example 3

Effect of Compound 14 on Mitosis in Mouse Lymphoma Cells

Compound 14 was dissolved in DMSO at 0.8 mM and 75 microliters ($\mu$L) of this solution was added to tubes containing 30 ml of cell suspension at $1.2 \times 10^5$ /mL grown under the conditions described in Example 1. Cells in control tubes received 75 $\mu$L of DMSO alone. Tubes were gassed with 5% $CO_2$, then incubated on a roller drum apparatus for 7 hours. The cells were treated with hypotonic medium (3-fold diluted growth medium) and fixed in acetic acid:methanol (1:3, v/v). After staining with aceto-orcein (method described in L. La Cour, *Stain Technology*, vol. 16, pp. 169–174 (1941)) the percentage of cells with visible chromosomes in treated and control cells was determined based on examination of 400 cells per sample. As shown in Table 10, compound 14 (2 $\mu$M produced an increase in the number of cells with visible chromosomes. As is typical for antimitotic compounds, normal mitotic figures, which were present in control cells with visible chromosomes, were lacking in the treated cells.

TABLE 10

Effect of compound 14 on mitosis in mouse lymphoma cells

| Treatment | Percentage of cells with visible chromosomes |
|---|---|
| None (control) | 3.9 |
| Compound 14 | 27.4 |

Example 4

Inhibition of Microtubule Assembly

Compounds were evaluated for their ability to inhibit tubulin assembly into microtubules by comparing the extent of cold-reversible assembly in the presence of each test compound with controls lacking the test compound. Tubulin was isolated from calf brain tissue by two cycles of assembly/disassembly as described by Vallee, R. B. in *Methods in Enzymology*, vol. 134, pp. 89–104. Assay mixtures contained 1 mg/ml of purified tubulin in 1 M sodium glutamate, pH 6.6, 1 millimolar (mM) $MgCl_2$, and the test compound, which was added as a solution in DMSO. The final concentration of DMSO in each assay was 2% (v/v). Assay mixtures were preincubated at 37° C. for 1 h, then chilled on ice for 5 min. Microtubule assembly was initiated by addition of guanosine triphosphate (0.1 mM), and incubation at 37° C. Assembly was followed turbidimetrically at 350 nm for 20 minutes (min) using a temperature-controlled cell in a Cary 2200 spectrophotometer. Since microtubules undergo depolymerization at 0° C., assembly was confirmed by measuring the reduction in turbidity following incubation for 30 min at 0° C. The difference in absorbance before and after incubation for 30 min at 0° C. ($\Delta A_{350}$) represents the extent of microtubule assembly. Inhibition of assembly was calculated by subtracting the ($\Delta A_{350}$) values for treatments with test compounds from the ($\Delta A_{350}$) for controls without test compound, and expressing this difference as a percentage of the ($\Delta A_{350}$) value for the control. Results including test compound number, test compound concentration in micromoles per liter ($\mu$M) and percent inhibition are set forth in Table 11.

TABLE 11

Inhibition of microtubule assembly by N-acetonylarylamides

| Compound | Concentration ($\mu$M) | Percent inhibition |
|---|---|---|
| 4 | 50 | 89.8 |
| 5 | 50 | 88.7 |
| 7 | 5 | 97.0 |
| 13 | 5 | 90.9 |
| 14 | 50 | 56.3 |
| 15 | 50 | 94.6 |
| 17 | 50 | 85.9 |
| 23 | 50 | 50.5 |
| 25 | 50 | 30.9 |
| 26 | 50 | 56.6 |
| 28 | 50 | 22.3 |
| 33 | 50 | 12.2 |
| 35 | 50 | 17.9 |
| 41 | 5 | 76.0 |
| 44 | 50 | 100.0 |

Example 5

Effect of Preincubation Time with Tubulin on Microtubule Assembly

The extent of inhibition of microtubule assembly by N-acetonylarylamides was found to be strongly dependent on the time of preincubation with tubulin. Compound 14 (16 $\mu$M) was preincubated with tubulin under the conditions described in Example 4 for 0, 1, 2, 4 and 6 hours before initiating assembly by addition of guanosine triphosphate (0.1 mM), and incubation at 37° C. Inhibition of assembly was determined as in Example 4, and results including preincubation time and percent inhibition of assembly are set forth in Table 12.

TABLE 12

Effect of preincubation time with tubulin on inhibition of microtubule assembly by compound 14

| Preincubation time (h) | Percent inhibition |
|---|---|
| 0 | 0 |
| 1 | 5.1 |
| 2 | 22.6 |
| 4 | 57.6 |
| 6 | 87.2 |

What is claimed is:

1. A method for inhibiting mammalian cell growth in benign or malignant tumors comprising treating said cells with an effective amount of a compound having the structural formula:

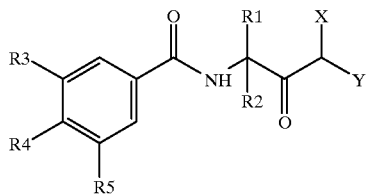

$R^1$ and $R^2$ are selected from the group consisting of H, $(C_1-C_6)$alkyl, halo$(C_1-C_6)$alkyl, $(C_2-C_6)$alkenyl, and $(C_2-C_6)$alkynyl, provided that at least one of $R^1$ and $R^2$ is not H; $R^3$, $R^4$, and $R^5$ are each independently selected from the group consisting of H, halo, cyano, $(C_1-C_6)$alkyl, halo$(C_1-C_6)$alkyl, $(C_2-C_6)$alkenyl, $(C_2-C_6)$alkynyl, $(C_1-C_6)$alkoxyl, $(C_1-C_6)$alkylthio, halo$(C_1-C_6)$alkoxyl, nitro, —$NR^6R^7$, —$CR^8$=$NOR^9$, $NHCOOR^{10}$, —$CONR^{11}R^{12}$, and —$COOR^{13}$, $R^6$, $R^7$, $R^8$, $R^9$, $R^{10}$, $R^{11}$, $R^{12}$, and $R^{13}$ are H or $(C_1-C_6)$alkyl; and X and Y are each independently selected from the group consisting of H, halo, cyano, thiocyano, isothiocyano and $(C_1-C_6)$alkylsulfonyloxy, provided that at least one of X and Y is halo, cyano, thiocyano, isothiocyano or $(C_1-C_6)$alkylsulfonyloxy and wherein said cells are sensitive to the compounds of the formula.

2. The method of claim 1 wherein X is chloro; Y is H; $R^1$ is methyl; $R^2$ is selected from methyl and ethyl; and $R^3$ and $R^5$ are each independently selected from H, halo, methyl, nitro, cyano, $NR^6R^7$, $CR^8$=$NOR^9$, and —$NHCOOR^{10}$; and $R^4$ is selected from H, $NR^6R^7$, cyano, —$CR^8$=$NOR^9$, $NHCOOR^{10}$, $COOR^{13}$, and $(C_1-C_4)$ alkyl, and $R^6$, $R^7$, $R^8$, $R^9$, $R^{10}$ and $R^{13}$ are H or $(C_1-C_6)$alkyl.

3. The method of claim 1 wherein X is chloro, Y is H, $R^1$ is methyl, $R^2$ is ethyl, $R^3$ is halo or cyano, $R^4$ and $R^5$ are selected from $NH_2$ and CH=$NOCH_3$, provided that $R^4$ and $R^5$ are not the same.

4. The method of claim 2 wherein the compound administered is selected from the group consisting of: 4-amino-3-chloro-5-methoxyiminomethyl-N-(3-chloro-1-ethyl-1-methyl-2-oxopropyl)benzamide; 3-chloro-5-cyano-N-(3-chloro-1-ethyl-1-methyl-2-oxopropyl)benzamide; and 5-bromo-N-(3-chloro-1-ethyl-1-methyl-2-oxopropyl)nicotinamide.

5. A method for controlling the growth of benign or malignant tumor cells in a subject having tumor cells, comprising administering to said subject an effective amount of the compound of claim 2 and wherein said cells are sensitive to the compounds of the formula.

* * * * *